US 9,895,337 B2

(12) United States Patent
Kim et al.

(10) Patent No.: US 9,895,337 B2
(45) Date of Patent: Feb. 20, 2018

(54) COMPOSITIONS CONTAINING MONOACETYLDIACYLGLYCEROL COMPOUND AS AN ACTIVE INGREDIENT FOR PREVENTING OR TREATING RHEUMATOID ARTHRITIS

(71) Applicants: ENZYCHEM LIFESCIENCES CORPORATION, Seoul (KR); KOREA RESEARCH INSTITUTE OF BIOSCIENCE AND BIOTECHNOLOGY, Daejeon (KR)

(72) Inventors: Jae Wha Kim, Daejeon (KR); Sei Ryang Oh, Daejeon (KR); Kyung Seop Ahn, Daejeon (KR); Ho Bum Kang, Daejeon (KR); Beom Su Park, Daejeon (KR); Tae Suk Lee, Daejeon (KR); Jong Koo Kang, Chungcheongbuk-do (KR); Young Sik Jung, Seoul (KR); Ki-Young Sohn, Seoul (KR)

(73) Assignees: Enzychem Lifesciences Corporation, Seoul (KR); Korea Research Institute of Bioscience and Biotechnology, Daejeon (KR)

(*) Notice: Subject to any disclaimer, the term of this patent is extended or adjusted under 35 U.S.C. 154(b) by 0 days.

(21) Appl. No.: 15/048,732

(22) Filed: Feb. 19, 2016

(65) Prior Publication Data
US 2016/0166528 A1 Jun. 16, 2016

Related U.S. Application Data
(63) Continuation of application No. PCT/KR2014/007631, filed on Aug. 18, 2014.

(30) Foreign Application Priority Data
Aug. 19, 2013 (KR) .................. 10-2013-0098186

(51) Int. Cl.
A61K 31/231 (2006.01)
A61K 9/00 (2006.01)
(Continued)

(52) U.S. Cl.
CPC .......... A61K 31/231 (2013.01); A61K 9/0053 (2013.01); A61K 9/4825 (2013.01); A61K 31/23 (2013.01)

(58) Field of Classification Search
CPC .... A61K 31/23; A61K 31/231; A61K 9/0053; A61K 9/4825
See application file for complete search history.

(56) References Cited

U.S. PATENT DOCUMENTS
7,662,853 B2 2/2010 Kim .............................. 514/547
2003/0166535 A1 9/2003 Podolsky ...................... 514/2.4
(Continued)

FOREIGN PATENT DOCUMENTS
EP 1900364 9/2013
KR 10-2000-0071887 11/2000
(Continued)

OTHER PUBLICATIONS
Kavanagh (Drugs Today 1999, 35(4-5): 275, abstract.*
(Continued)

Primary Examiner — Savitha Rao
(74) Attorney, Agent, or Firm — Dentons US LLP; Stephanie Seidman

(57) ABSTRACT

The invention relates to pharmaceutical compositions, as well as health functional food compositions and quasi-drug compositions, for preventing, treating, or improving rheumatoid arthritis, comprising a monoacetyldiacylglycerol compound as an active ingredient. The monoacetyldiacylglycerol of the invention is effective in inhibiting the phosphorylation of STAT-3 known to be a therapeutic target for
(Continued)

(A) U937 15min
p-STAT3
STAT3
IL-6 -  +    +   +  +  + (10 ng/ml)
EC-18 - -  0.01 0.1  1  10 ug/ml (B) U937 60min
p-STAT3
STAT3
IL-6 -  +    +    +   +  + (10 ng/ml)
EC-18 - -  0.001 0.01 0.1 1  ug/ml rheumatoid arthritis. As the monoacetyldiacylglycerol is an effective therapeutic agent without toxicity, the monoacetyldiacylglycerol can overcome the side effects of the medicines currently used in the treatment of rheumatoid arthritis. Thus, the monoacetyldiacylglycerol can be used for preventing, treating or improving rheumatoid arthritis.

11 Claims, 6 Drawing Sheets

(51) Int. Cl.
    *A61K 9/48* (2006.01)
    *A61K 31/23* (2006.01)

(56) References Cited

U.S. PATENT DOCUMENTS

| | | | |
|---|---|---|---|
| 2004/0029893 A1 | 2/2004 | Lane | 514/254.07 |
| 2008/0194877 A1 | 8/2008 | Letari et al. | 564/271 |
| 2008/0200543 A1* | 8/2008 | Kim | A61K 31/22 514/547 |
| 2009/0253923 A1 | 10/2009 | Lee et al. | 554/79 |
| 2010/0035989 A1 | 2/2010 | Schwartz et al. | 514/560 |
| 2010/0137435 A1 | 6/2010 | Kim | 514/546 |
| 2010/0279959 A1 | 11/2010 | Gagnon et al. | 514/25 |
| 2014/0171438 A1 | 6/2014 | Pan et al. | 514/252.11 |
| 2016/0128966 A1 | 5/2016 | Han et al. | 514/183 |
| 2016/0151323 A1 | 6/2016 | Han et al. | 514/183 |
| 2017/0128404 A1 | 5/2017 | Sohn | 424/78.02 |

FOREIGN PATENT DOCUMENTS

| | | |
|---|---|---|
| KR | 10-2005-0103259 | 10/2005 |
| KR | 10-2006-0047447 | 5/2006 |
| KR | 10-2007-0010841 | 1/2007 |
| WO | WO 1999/026640 | 6/1999 |
| WO | WO 2005/112912 | 12/2005 |
| WO | WO 2015/026114 | 2/2015 |

OTHER PUBLICATIONS

Kim, Myung-Hwan et al., "EC-18, a synthetic monoacetyldiacylglyceride, inhibits hematogenous metastasis of KIGB-5 biliary cancer cell in hamster model," *Journal of Korean Medical Science*, 2009, vol. 24, pp. 474-480.
Letter/Written Disclosure of the Supplemental Information Disclosure Statement for the above-referenced application, filed herewith on Aug. 11, 2017, 2 pages.
Al-Tonbary et al., "Vitamin E and N-Acetylcysteine as Antioxidant Adjuvant Therapy in Children with Acute Lymphoblastic Leukemia," Advances in Hematology, vol. 2009, Article ID 689639, 5 pages (2009).
Cao, J. and E. Meighen, "Purification and structural identification of an autoinducer for the luminescence system of Vibrio harveyi," JBC 264:21670-21676 (1989).
Chang et al., "From hematopoietic stem cells to platelets," J. Thromb. and Haemost. 5(Suppl. 1):318-327 (2007).
Gomez et al., "Blockade of Chemotherapy-Induced Thrombocytopenia by Bax Inhibiting Peptides (BIPs) in Mouse Model," Blood 110:281 (2007). Abstract, 2 pages.
Jones et al., "A randomised pilot Phase II study of doxorubicin and cyclophosphamide (AC) or epirubicin and cyclophosphamide (EC) given 2 weekly with pegfilgrastim (accelerated) vs 3 weekly (standard) for women with early breast cancer," Brit. J. Cancer 100:305-310 (2009).
Kim et al., "Auranofin blocks interleukin-6 signalling by inhibiting phosphorylation of JAK1 and STAT3," Immunology 122(4): 607-614 (2007).
Machine generated English translation of the previously provided Korean Publication No. KR 10-2005-0103259, published Oct. 27, 2005, accessed from Espacenet on Jun. 29, 2017, 15 pages.
Morstyn et al., "Treatment of chemotherapy-induced neutropenia by subcutaneously administered granulocyte colony-stimulating factor with optimization of dose and duration of therapy," J. Clin. Oncol. 7(10):1554-1562 (1989). Abstract, 2 pages.
Wambi et al., "Dietary Antioxidants Protect Hematopoietic Cells and Improve Animal Survival after Total-Body Irradiation," Radiat. Res. 169(4):384-396 (2008).
Zuckerman, "Hematopoietic Abnormalities in Patients With Cancer," Cancer Control J. Suppl. 5(2 Suppl 1):1-4 (1998).
Office Action, dated Sep. 22, 2016, in connection with related U.S. Appl. No. 14/936,464, 16 pages.
Response, dated Jan. 23, 2017, to Office Action, dated Sep. 22, 2016, in connection with related U.S. Appl. No. 14/936,464, 39 pages.
Final Office Action, dated Apr. 4, 2017, in connection with related U.S. Appl. No. 14/936,464, 20 pages.
Request for Continued Examination and Preliminary Amendment, filed Aug. 4, 2017, responsive to the Final Office Action, dated Apr. 4, 2017, in connection with related U.S. Appl. No. 14/936,464, 22 pages.
International Search Report and Written Opinion, dated Aug. 5, 2015, in connection with related International Patent Application No. PCT/US2015/031204, 10 pages.
International Preliminary Report on Patentability, dated Nov. 15, 2016, in connection with related International Patent Application No. PCT/US2015/031204, 8 pages.
Examination Report, dated Jun. 9, 2017, in connection with related Australian Patent Application No. 2015258840, 5 pages.
Office Action, dated Sep. 22, 2016, in connection with related U.S. Appl. No. 14/951,353, 16 pages.
Response, dated Jan. 23, 2017, to Office Action, dated Sep. 22, 2016, in connection with related U.S. Appl. No. 14/951,353, 41 pages.
Final Office Action, dated Apr. 4, 2017, in connection with related U.S. Appl. No. 14/951,353, 15 pages.
Request for Continued Examination and Preliminary Amendment, filed Aug. 4, 2017, responsive to the Final Office Action, dated Apr. 4, 2017, in connection with related U.S. Appl. No. 14/951,353, 17 pages.
Office Action, dated May 19, 2016, in connection with related U.S. Appl. No. 14/959,750, 33 pages.
Response, filed Aug. 19, 2016, to Office Action, dated May 19, 2016, in connection with related U.S. Appl. No. 14/959,750, 7 pages.
Final Office Action, dated Dec. 29, 2016, in connection with related U.S. Appl. No. 14/959,750, 29 pages.
Request for Continued Examination and Preliminary Amendment, filed Jun. 29, 2017, responsive to the Final Office Action, dated Dec. 29, 2016, in connection with related U.S. Appl. No. 14/959,750, 18 pages.
Notice of Allowance, dated Jul. 28, 2017, in connection with related U.S. Appl. No. 14/959,750, 13 pages.
International Search Report and Written Opinion, dated Dec. 17, 2014, in connection with corresponding International Patent Application No. PCT/KR2014/007631, 8 pages.
International Preliminary Report on Patentability, dated Feb. 23, 2016, in connection with corresponding International Patent Application No. PCT/KR2014/007631, 7 pages.
Examination Report, dated Sep. 5, 2016, in connection with corresponding Australian Patent Application No. 2014309637, 3 pages.
Response, filed Jan. 23, 2017, to Examination Report, dated Sep. 5, 2016, in connection with corresponding Australian Patent Application No. 2014309637, 19 pages.
Examination Report, dated Feb. 10, 2017, in connection with corresponding Australian Patent Application No. 2014309637, 3 pages.
Response, filed Apr. 21, 2017, to Examination Report, dated Feb. 10, 2017, in connection with corresponding Australian Patent Application No. 2014309637, 16 pages.

(56) References Cited

OTHER PUBLICATIONS

Notice of Acceptance, dated May 8, 2017, in connection with corresponding Australian Patent Application No. 2014309637, 3 pages.
Examination Search Report, dated May 4, 2017, in connection with corresponding Canadian Patent Application No. 2921845, 3 pages.
Extended European Search Report, dated Mar. 24, 2017, in connection with corresponding European Patent Application No. 14837360.8, 5 pages.

* cited by examiner

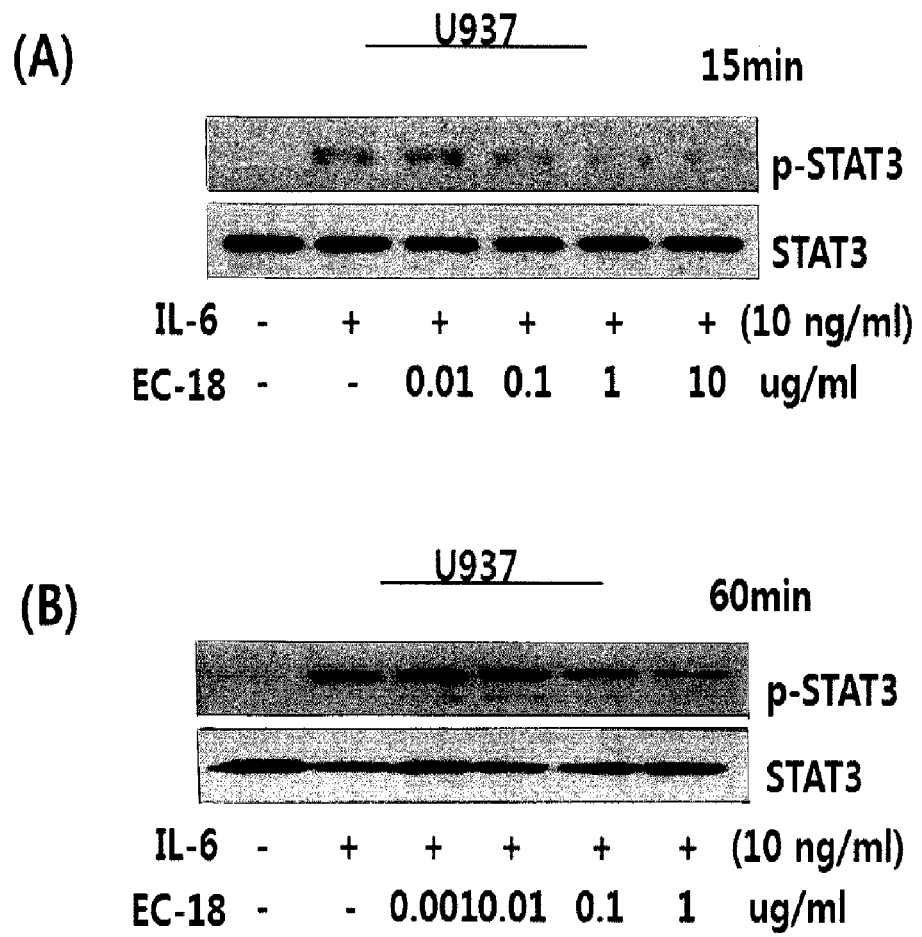
[Fig. 1]

[Fig. 2]
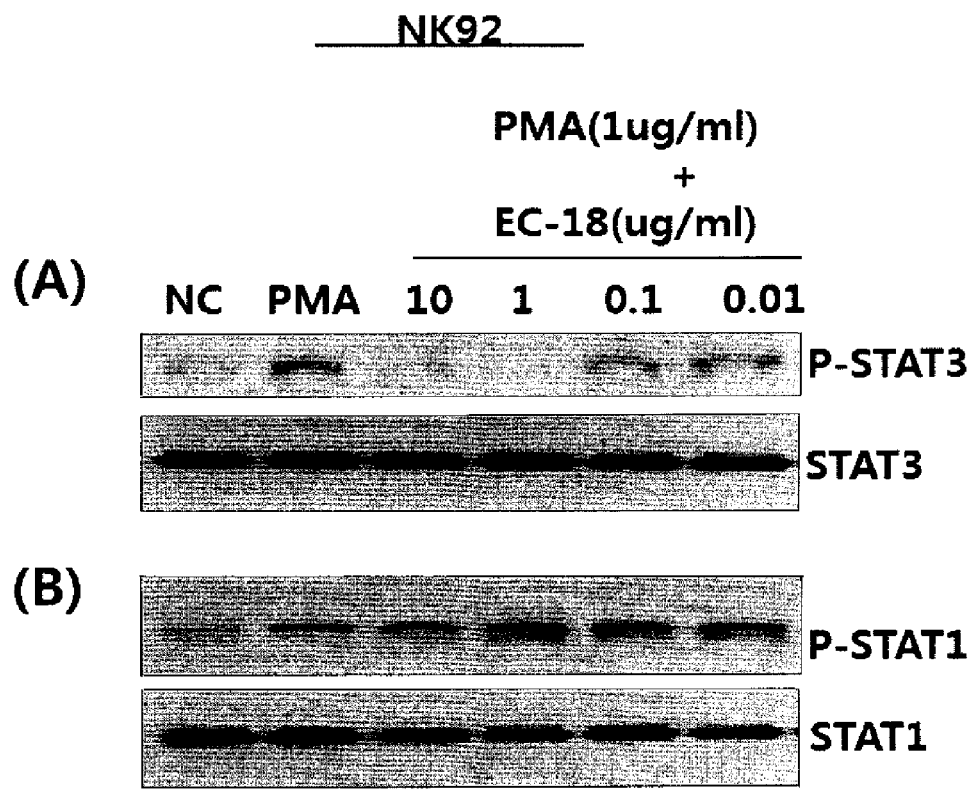
<Western Blot>
NC; negative control
PMA: Phorbol 12-myristate 13-acetate

[Fig. 3]
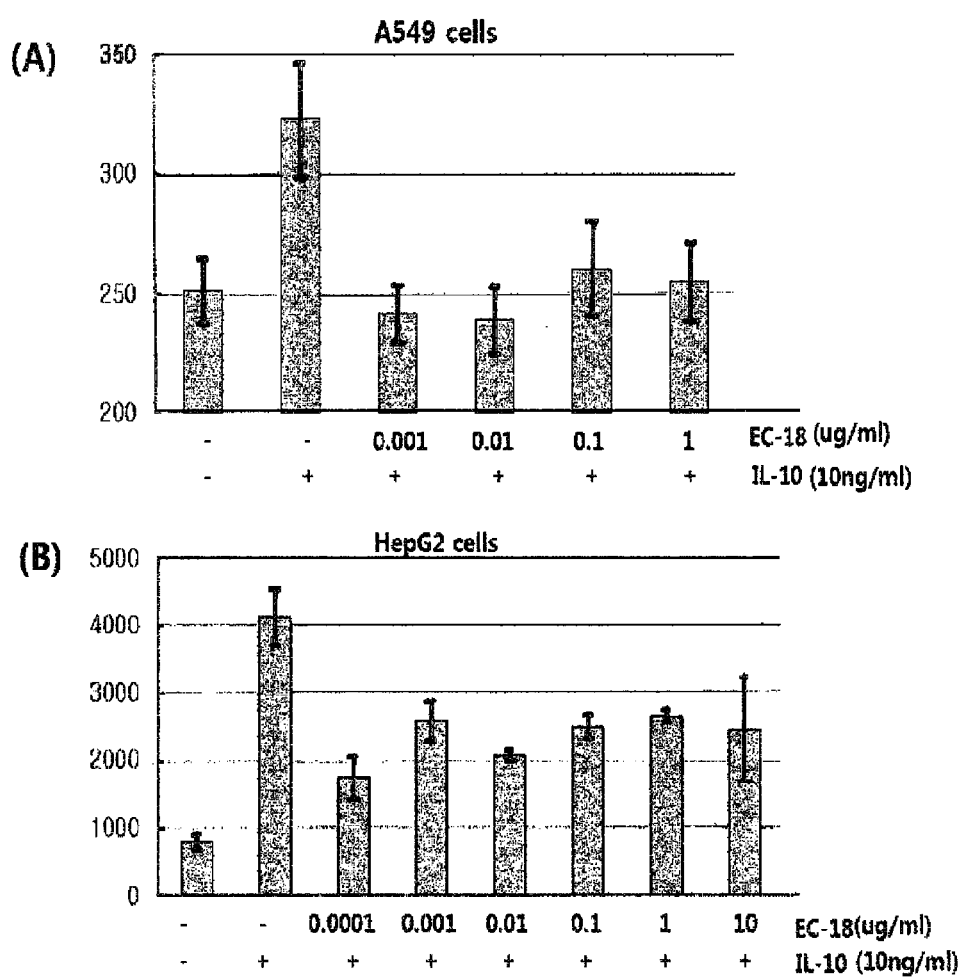

[Fig. 4]
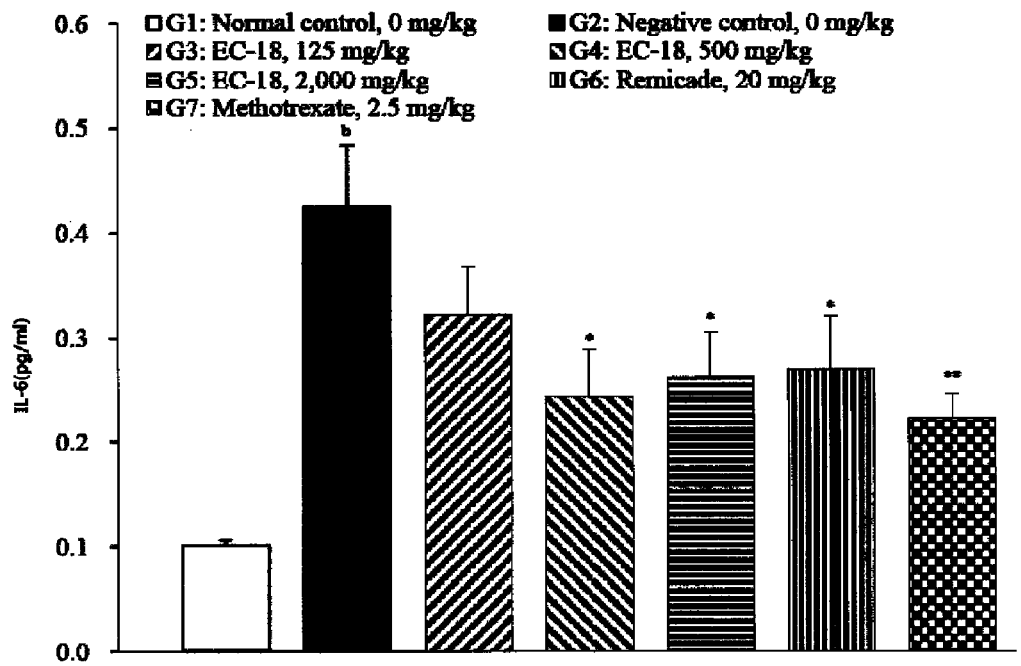
[Fig. 5]
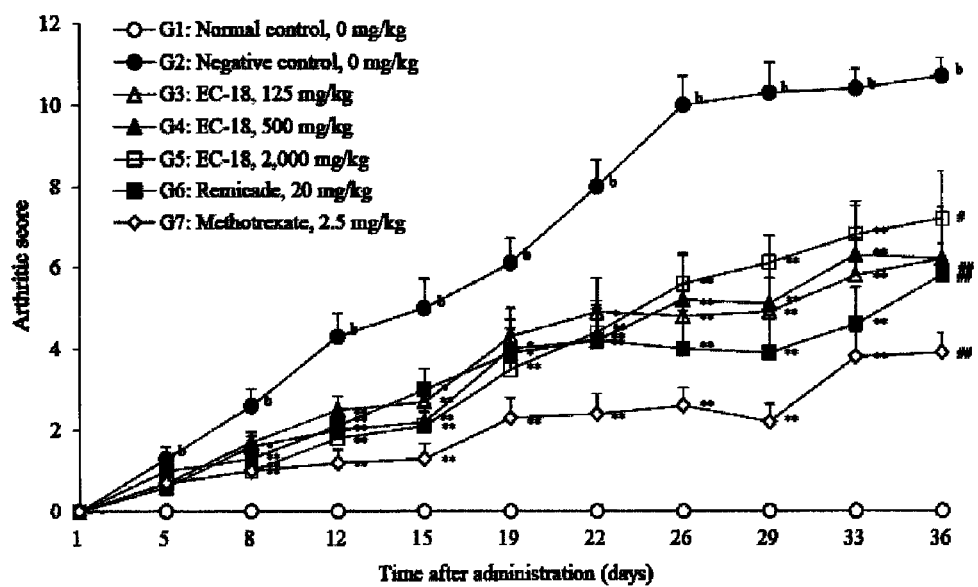

[Fig. 6]
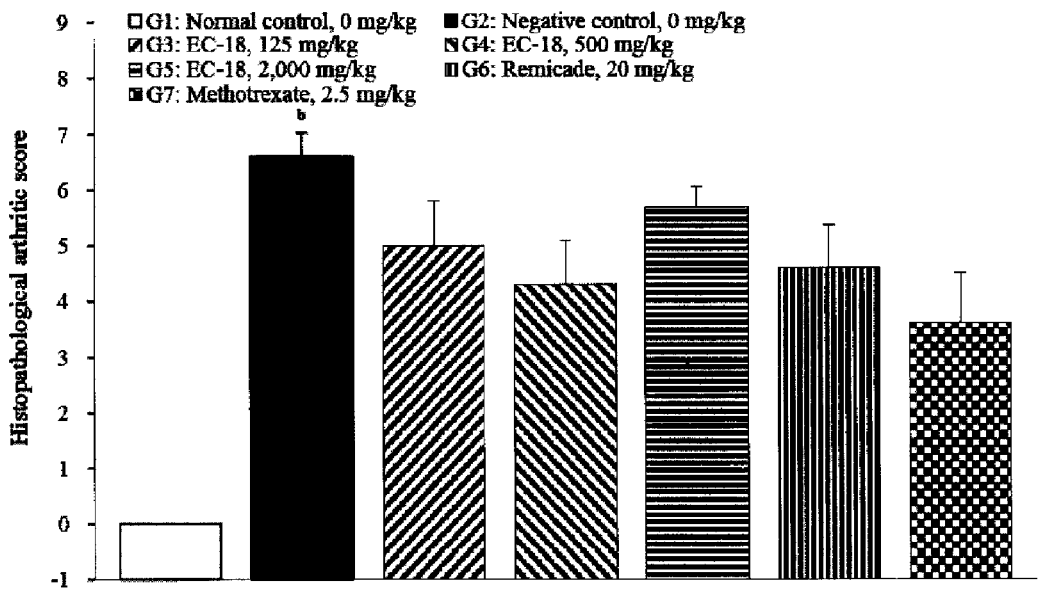
[Fig. 7]
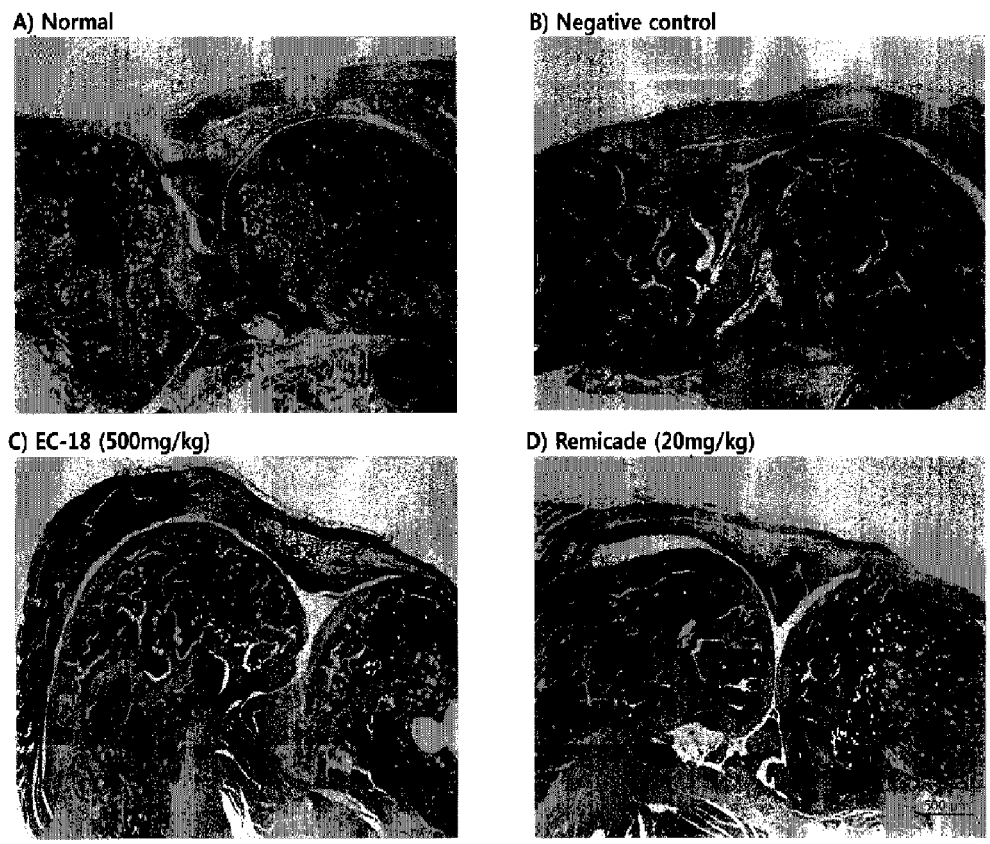
C: cartilage, S: synovial membrane, TB: trabecular bone, CB: compact bone, BM: bone marrow, GP: growth plate, star(*): Pannus

[Fig. 8]
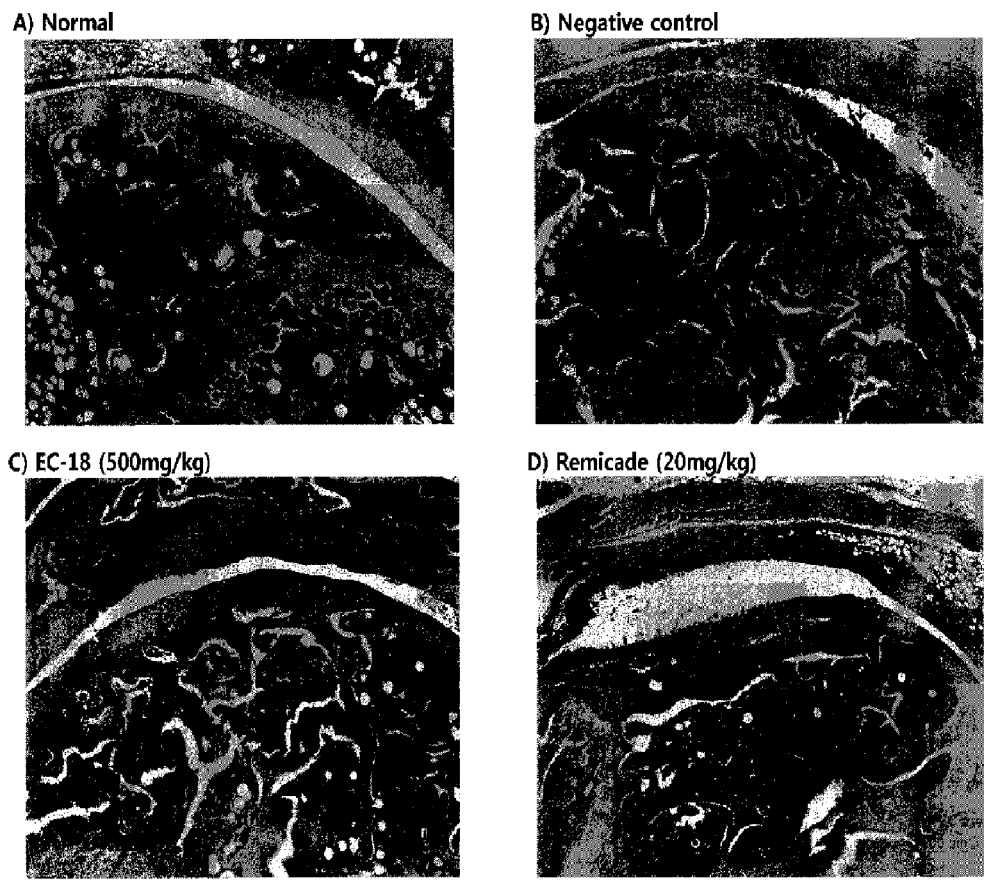
C: cartilage, S: synovial membrane, TB: trabecular bone, BM: bone marrow, GP: growth plate, star(*): Pannus, Arrow (↓): Articular cartilage destruction and bone erosion, , star(*): Pannus

COMPOSITIONS CONTAINING MONOACETYLDIACYLGLYCEROL COMPOUND AS AN ACTIVE INGREDIENT FOR PREVENTING OR TREATING RHEUMATOID ARTHRITIS

FIELD OF THE INVENTION

The present invention relates to pharmaceutical compositions, as well as health functional food compositions and quasi-drug compositions, for preventing, treating, or improving rheumatoid arthritis, comprising a monoacetyldiacylglycerol compound as an active ingredient.

BACKGROUND OF THE INVENTION

Rheumatoid arthritis is a chronic autoimmune disease that causes inflammation by attacking joints or other parts of the body. Rheumatoid arthritis causes a painful swelling of fingers, hands, feet, wrists, ankles, knees and sometimes can affect other organs of the body such as muscle, skin, lungs and eyes. The underlying cause of rheumatoid arthritis remains unclear and has been investigated continuously. To date, known methods for treating or preventing rheumatoid arthritis are not effective and better treatments are needed. Many hormone medications such as steroids have been widely used to treat arthritis. However, because the use of the hormone medications is not a fundamental treatment and can cause several side effects, the treatment is limited. Arthritis, especially rheumatoid arthritis, causes severe pain so that the patient must take anti-inflammatory agents. Aspirine has been widely used to alleviate the pain for a long time. However, the harmful effect of aspirine on stomach makes it difficult to take a sufficient amount of aspirine necessary for the treatment of arthritis continuously.

Drugs currently used for the treatment of arthritis have several limitations including side effects preventing long-term use of the drugs, the absence of anti-inflammatory effect and the lack of efficacy for treating the arthritis that has already occurred. As a solution of this problem, the development of an effective therapeutic agent for arthritis has been constantly needed. Most of currently used medications for treating arthritis have a certain degree of side effect, although it is varied among medications and patients. Especially, because it is necessary to take medications for a long period of time for the treatment of rheumatoid arthritis, it is very important and urgent problem to develop a novel pharmaceutic agent with low side effect.

EC 18 is a monoacetyldiglyceride and has been separated from deer antler. It has been reported that EC-18 increases survivability ratio of animals in sepsis animal model experiment using cecal-ligation-puncture, and shows no toxicity in a GLP (Good Laboratory Practice) toxicity test. However, the effect of the monoacetyldiacylglycerol compounds including EC-18 on rheumatoid arthritis is not known or disclosed in the prior art. Thus the present inventors aimed to find a compound derived from natural products or a novel compound for the treatment of rheumatoid arthritis and found that the monoacetyldiacylglycerol compound inhibits STAT-3, a therapeutic target for rheumatoid arthritis and can be used to prevent or treat rheumatoid arthritis.

DETAILED DESCRIPTION OF THE INVENTION

Technical Problem

An object of the present invention is to provide pharmaceutical compositions, health functional food compositions and quasi-drug compositions, for preventing, treating, or improving rheumatoid arthritis, comprising a monoacetyldiacylglycerol of Formula 1 as an active ingredient.

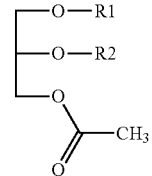

[Formula 1]

wherein $R_1$ and $R_2$ are independently a fatty acid residue of 14 to 20 carbon atoms.

Another object is to provide methods for preventing or treating rheumatoid arthritis, comprising administering a compound of formula 1 to a patient that suffers from rheumatoid arthritis or can develop rheumatoid arthritis.

Technical Solution

In some embodiments for achieving the above objects, the present invention provides pharmaceutical compositions for preventing or treating rheumatoid arthritis, comprising a monoacetyldiacylglycerol of Formula 1 as an active ingredient.

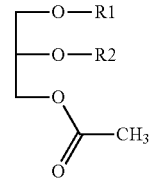

[Formula 1]

wherein $R_1$ and $R_2$ are independently a fatty acid residue of 14 to 20 carbon atoms. In the present disclosure, fatty acid residue refers to the acyl moiety resulting from formation of an ester bond by reaction of a fatty acid and an alcohol.

Specifically, the pharmaceutical composition for preventing or treating rheumatoid arthritis of the present invention comprises a monoacetyldiacylglycerol of Formula 1. In the present disclosure, the term "monoacetyldiacylglycerol compound" means a glycerol derivative containing an acetyl group and two acyl groups and is also referred to as MADG.

In the monoacetyldiacylglycerol derivatives of Formula 1, $R_1$ and $R_2$ are independently a fatty acid residue of 14 to 20 carbon atoms. Non-limiting examples of $R_1$ and $R_2$ thus include palmitoyl, oleoyl, linoleoyl, linolenoyl, stearoyl, myristoyl, arachidonoyl, and so on. Preferable combinations of $R_1$ and $R_2$ ($R_1/R_2$) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyldiacylglycerol derivatives of Formula 1 can be (R)-form, (S)-form or a racemic mixture, and may include their stereoisomers.

In one embodiment, the monoacetyldiacylglycerol is a compound of the following Formula 2:

[Formula 2]

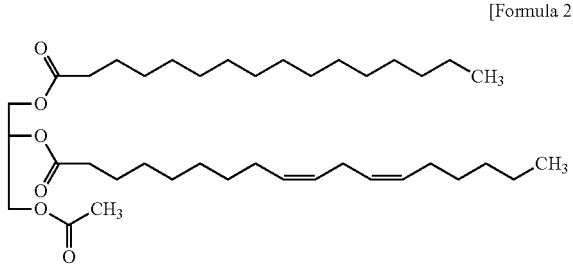 [SMILES: CCCCC/C=C\C/C=C\CCCCCCCC(=O)OC(COC(C)=O)COC(=O)CCCCCCCCCCCCCCC]

The compound of Formula 2 is 1-palmitoyl-2-linoleoyl-3-acetylglycerol, sometimes referred as "EC-18" in this disclosure. $R_1$ and $R_2$ of the compound of Formula 2 are palmitoyl and linoleoyl, respectively.

The monoacetyldiacylglycerol compounds can be separated and extracted from the natural deer antler or can be produced by known organic synthesis methods (Korean Registered Patents No. 10-0789323). More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacylglycerol compound for the present invention. A solvent for the extraction is selected among chloroform/methanol, hexane/ethylacetate/acetic acid, but not limited thereto.

A chemical synthetic method for the preparation of monoacetyldiacylglycerol compounds is shown in Korean Registered Patents No. 10-0789323. Specifically, the method comprises (a) a step of preparing 1-R1-3-protecting group-glycerol by adding a protecting group in the position 3 of 1-R1-glycerol; (b) a step of preparing 1-R1-2-R2-3-protecting group-glycerol by introducing R2 in the position 2 of the 1-R1-3-protecting group-glycerol; and (c) a step of preparing the desired monoacetyldiacylglycerol compound by performing a deprotection reaction and the acetylation reaction of the 1-R1-3-protecting group-glycerol at the same time. The monoacetyldiacylglycerol compound may be further purified if necessary. Alternatively, monoacetyldiacylglycerol compounds can be prepared by acid decomposition of phosphatidylcholine (acetolysis) but is not limited thereto. Stereoisomers of the compounds of formula (I) are also within the scope of the invention.

In the present disclosure, it is shown that the monoacetyldiacylglycerol compound inhibits the phosphorylation of STAT-3, thus effective in preventing or treating rheumatoid arthritis.

In the disclosure, the term "rheumatoid arthritis" is a chronic inflammatory disease of unknown cause characterized by polyarthritis Inflammation initially appears in the synovium surrounding the joint but gradually spreads to the periphery of the cartilage and bone, leading to damage and deformity of the joint. In addition to the joint, rheumatoid arthritis can attack other body parts. The symptoms of rheumatoid arthritis include anemia, dry syndromes, subcutaneous nodules, pulmonary fibrosis, vasculitis and skin ulcers. Medicines used for the treatment of rheumatoid arthritis include nonsteroidal anti-inflammatory agents, steroids, an anti-rheumatic drug and TNF blocking agents, but are known to present a risk of various side effects. As used herein, the term "prevention" or "preventing" includes any activity to suppress or delay the onset of rheumatoid arthritis by administering the composition of the present invention. The term "treatment" or "treating" includes prophylaxis, mitigation, amelioration, delay or reduction of symptoms, as well as partial or complete elimination or prevention of symptoms, of rheumatoid arthritis by administering the composition of the present invention.

It has been recently found that Th17 cells that produce interleukin-17 (IL-17) play a leading role in the pathogenesis of rheumatoid arthritis. Especially, Th17 cells induce joint inflammation and bone destruction directly. Specifically, STAT-3 known as a key transcription factor for the differentiation and the activity of Th17 cells can regulate the locus of IL-17 and play an essential role in the expression of many transcriptional factors involved in the differentiation of TH17 cells. STAT-3 can be activated by a phosphorylation. It has been known that the inhibition of STAT-3 activation in TH17 cells can control TH17 cells and increase the activity of immunoregulatory T cells, thus preventing or treating rheumatoid arthritis. Thus, STAT-3 has become a therapeutic target for rheumatoid arthritis.

In the examples of the present disclosure, it is shown that (i) in U937 and NK-92 cells where STAT-3 is activated by the treatment of IL-6 and PMA (Phorbol 12-myristate 13-acetate), respectively, EC-18 inhibits the phosphorylation of STAT-3 in a concentration-dependent manner (Experiment 1 and 2, FIGS. 1 and 2), and (ii) in A549 and HepG2 cells where STAT-3 is activated by the treatment of IL-10, EC-18 inhibits the phosphorylation of STAT (Example 3, FIG. 3). These results show that the monoacetyldiacylglycerol compound is effective in treating rheumatoid arthritis. In the example of animal model in which arthritis is induced by collagen, arthritis index determined by the examination with the naked eye (Example 4, FIG. 5) and IL-6 concentration in the serum (Example 4, FIG. 4) are significantly decreased compared to the negative control group. Tissue staining result also shows that EC-18 in the concentration of 125, 500 and 2,000 mg/kg is effective in improving the symptoms of collagen-induced arthritis (Example 4, FIGS. 6 and 7).

The pharmaceutical composition comprising a monoacetyldiacylglycerol of the invention may include conventional pharmaceutically acceptable carriers, excipients, or diluents. The amount of monoacetyldiacylglycerol in the pharmaceutical composition can be widely varied without specific limitation, and is specifically 0.0001 to 100 weight %, preferably, 0.001 to 50 weight %, more preferably 0.01 to 20 weight %, with respect to the total amount of the composition.

The pharmaceutical composition may be formulated into solid, liquid, gel or suspension form for oral or non-oral administration, for example, tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as fillers, bulking agents, binders, wetting agents, disintegrating agents, and surfactants can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various excipients such as wetting agents, sweeting agents, flavoring agents, and preserving agents. The formulation for non-oral administration includes sterilized aqueous solution, non-aqueous solution, freeze-dried formulation, suppository, and so on, and solvent for such solution may include propylene glycol, polyethylene glycol, vegetable oils such as olive oil, and ester for syringe injection such as ethyl oleate. Base materials of the suppository may include witepsol, macrogol, tween 61, cacao butter, Laurin and glycerogelatin.

The monoacetyldiacylglycerol compound can be administered in a pharmaceutically effective amount. The term "pharmaceutically effective amount" is used to refer to an amount that is sufficient to achieve a desired result in a medical treatment. The "pharmaceutically effective amount" can be determined according to the subject's category, age, sex, severity and type of disease, activity of drug, sensitivity to drug, administration time, administration route, excretion rate, and so forth. The composition of the present invention can be administered alone or with other therapeutic agents sequentially or simultaneously. The composition of the present invention can be administered once or multiple times. The preferable amount of the composition of the present invention can be varied according to the condition and weight of patient, severity of disease, formulation type of drug, administration route and period of treatment. An appropriate total amount of administration per 1 day can be determined by a physician, and is generally about 0.001 to about 1000 mg/kg, preferably about 0.05 to 200 mg/kg, more preferable about 0.1 to about 100 mg/kg once a day or can be administered in divided doses multiple times daily. The composition of the present invention can be administered to any subject that requires the prevention or treatment of rheumatoid arthritis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous (i.v.), intramuscular (i.m.), subcutaneous (s.c.), intra-uterine dural or cerebrovascular injection.

In some embodiments, the present invention provides health functional food compositions for preventing or improving rheumatoid arthritis, which comprises a monoacetyldiacylglycerol of formula 1 as an active ingredient:

[Formula 1]

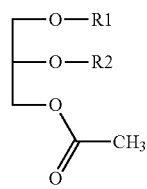

wherein $R_1$ and $R_2$ are independently a fatty acid residue of 14 to 20 carbon atoms, but are not limited thereto.

Specifically, the monoacetyldiacylglycerol of the invention can be included in health functional food compositions for preventing or improving rheumatoid arthritis. The monoacetyldiacylglycerol and rheumatoid arthritis are the same as explained above. The term "improvement" or "improving" includes any activity to improve or ameliorate the symptoms of rheumatoid arthritis by administering the composition of the present invention.

The health functional food composition of the present invention for preventing or improving rheumatoid arthritis may consist of only or substantially pure monoacetyldiacylglycerols, or may include the monoacetyldiacylglycerol and other conventional ingredients of health functional food. The amount of monoacetyldiacylglycerol in the health food composition can be determined suitably according to the intended use. Generally, the amount of monoacetyldiacylglycerol is preferably less than 15 weight %, more preferably less than 10 weight %, with respect to the total amount of the health functional food composition when the monoacetyldiacylglycerol is included in food or beverages. However, the amount of monoacetyldiacylglycerol may be increased or decreased. In case of a long term use for the purpose of the health control and hygiene, the amount of the monoacetyldiacylglycerol can be less than the above range. Since there is no problem in terms of safety, the monoacetyldiacylglycerol may be used in an amount greater than the above range.

Foods to which the compound of the present invention can be added are not limited and include various foods, for example, meats, sausages, breads, chocolates, candies, snacks, pizzas, noodles, gums, daily products such as ice creams, soups, beverages, teas, drinks, alcoholic beverages, vitamin complexes and any health functional food. When the monoacetyldiacylglycerol is used in the beverage product, the beverage product may include sweeting agents, flavoring agents or carbohydrates. Examples of carbohydrates include monosaccharides such as glucose and fructose, disaccharides such as maltose and sucrose, polysaccharides such as dextrin and cyclodextrin, and sugar alcohols such as xylitol, sorbitol and erythritol. The amount of carbohydrate in the beverage composition can be widely varied without specific limitation, and is preferably 0.01 to 0.04 g, more preferably, 0.02 to 0.03 g per 100 ml of the beverage. Examples of sweeting agents include natural sweeteners such as thaumatin and stevia extract and artificial sweeteners such as saccharin and aspartame. In addition to the above, the health functional food composition of the present invention may include various nutrients, vitamins, electrolytes, flavoring agents, colorants, pectic acid and salts thereof, alginic acid and salts thereof, organic acids, protective colloidal thickening agents, pH controlling agents, stabilizing agents, preserving agents, glycerin, alcohol, carbonizing agents used in carbonated beverages and so on. Moreover, the health functional food composition of the present invention may include fruits, as used in preparing natural fruit juices and fruit juice beverages and vegetable beverages.

In some embodiments, the present invention provides quasi-drug compositions for preventing or improving rheumatoid arthritis, which comprises a monoacetyldiacylglycerol of formula 1 as an active ingredient:

[Formula 1]

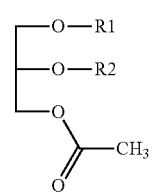

wherein $R_1$ and $R_2$ are independently a fatty acid residue of 14 to 20 carbon atoms, but are not limited thereto.

Specifically, the monoacetyldiacylglycerol of the invention can be included in quasi-drug compositions for preventing or improving rheumatoid arthritis.

The term "quasi-drug" means a product which falls under any of the followings: (a) Fibers, rubber products or similar products used for the purpose of treating, alleviating, or preventing human or animal diseases; (b) Non-appliance, non-machinery or similar products which have insignificant influences on or do not directly act upon human bodies; and (c) Preparations used for sterilization, insecticide and purposes similar thereto in order to prevent communicable diseases. However, the term "quasi-drug" does not include (a) products used for the purposes of diagnosis, medical care, alleviation, treatment or prevention of diseases of human beings or animals, excluding appliances, machinery and equipment; or (b) products, other than appliances, machinery or equipment, used for the purpose of exerting pharmacological effects upon the structure or functions of human beings or animals. Quasi-drugs include the external preparations for skin and personal care products.

The quasi-drug composition of the present invention for preventing or improving rheumatoid arthritis may consist of only or substantially pure monoacetyldiacylglycerols, or may include the monoacetyldiacylglycerol and other conventional ingredients of quasi-drugs. The amount of monoacetyldiacylglycerol in the quasi-drug composition can be determined suitably in accordance with the intended use. The skin external preparations to which the compound of the present invention can be added include, for example, ointments, lotions, spray agents, patches, creams, powders, suspensions, and gels but are not limited thereto.

In some embodiments, the present disclosure provides methods for preventing or treating rheumatoid arthritis, comprising administering a composition comprising a compound of formula 1 to a patient in need thereof. The term "patient in need" includes any animal including human that suffers from rheumatoid arthritis or can develop rheumatoid arthritis. Rheumatoid arthritis can be treated or prevented by administering an effective amount of a compound of formula 1 to a patient in need thereof. The term "administration" means introducing the pharmaceutical composition of the present invention to a patient in need by any suitable method. The composition of the present disclosure can be administered by conventional various methods, for example, by oral or non-oral administration.

In some embodiments, the present disclosure provides methods for preventing or treating rheumatoid arthritis, comprising administering an effective amount of a pharmaceutical composition comprising a compound of formula 1 to a patient in need thereof. An appropriate total amount of administration per 1 day can be determined by a physician, and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of the monoacetyldiacylglycerol administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

Technical Effects

The monoacetyldiacylglycerol of the invention is effective in inhibiting the phosphorylation of STAT-3 known to be a therapeutic target for rheumatoid arthritis. As the monoacetyldiacylglycerol is an effective therapeutic agent without toxicity, the monoacetyldiacylglycerol can overcome the side effects of the medicines currently used in the treatment of rheumatoid arthritis. Thus, the monoacetyldiacylglycerol can be used for preventing, treating or improving rheumatoid arthritis.

BRIEF DESCRIPTION OF THE DRAWINGS

FIG. 1 is the result of western blot analysis showing the inhibition of STAT-3 phosphorylation induced by IL-6 in U937 cells with the treatment of EC-18 in different concentrations. In (A), EC-18 is treated for 15 minutes. In (B) EC-18 is treated for 60 minutes.

FIG. 2 is the result of western blot analysis showing the inhibition of STAT-3 phosphorylation (A) and STAT-1 phosphorylation (B) induced by PMA (Phorbol 12-myristate 13-acetate) in NK-92 cells with the treatment of EC-18 in different concentrations.

FIG. 3 is the result of luciferase fluorescence representing STAT-3 activity in A549 cells (A) and HepG2 cells (B).

FIG. 4 is the measurement of the concentration of interleukin-6 in serum corrected at the day of tissue excision in normal group, negative control group, EC-18 treatment groups and positive control group.

FIG. 5 is arthritis score measured by the examination with the naked eye in normal group, negative control group, EC-18 treatment groups and positive control group.

FIG. 6 is the result of histopathological arthritis score of knee joint in normal group, negative control group, EC-18 treatment groups and positive control group.

FIGS. 7 and 8 show microscopic images of stained arthritic tissue in normal group, negative control group, EC-18 treatment groups and positive control group.

EXAMPLES

The following examples are provided for better understanding of this invention. However, the present invention is not limited by the examples.

Example

Cell Culture

Human cell lines NK-92, U937, A549 and HepG2 (American Type Culture Collection, ATCC, Rockville, Md.) were cultured at 37° C. under 5% $CO_2$ humid conditions. NK-92 cells were cultured in alpha-MEM media (Life Technologies, Karlsruhe, Germany) containing 10% Fetal Calf Serum (FCS, HyClone, Logan, Utah), 2 mM L-glutamate, 100 μg/ml penicillin, 100 μg/ml streptomycin (Life Technologies). U937, A549 and HepG2 cells were cultured in RPMI media containing 10% Fetal Calf Serum.

Experimental Example 1

Inhibitory Effect of EC-18 on STAT-3 Phosphorylation in U937 Cells

Cells treated in EC-18 and IL-6 cytokines were lysed with cold SDS lysis buffer [(50 mM HEPES, 150 mM NaCl, 0.2 mM EDTA, 0.5% NP-40, 0.1% SDS, 1 mM $Na_3VO_4$, 10 mM NaF, and complete Protein Inhibitor Cocktail (Roche)] for 30 minutes on ice. After cell lysis, the aqueous solution was separated from the insoluble precipitate by centrifuging the cell lysates for 30 minutes at 13,000 rpm in a high-speed centrifuge. After protein quantification, the aqueous solution was separated in 10 to 12% SDS-PAGE by electrophoresis. Proteins separated in the gel were transferred into PVDF membrane (Millipore, Billerica, Mass., USA) at 100V for 2 hours.

To measure the amount of phosphorylated STAT-3, the membrane was incubated with poly rabbit-anti-(STAT1, STAT3) or poly rabbit-anti-phospho (STAT1, STAT3) antibody (Cell Signaling Technology, USA (1:1000) as a primary antibody for 60 minutes at room temperature. The membrane was incubated with horseradish peroxidase-conjugated goat anti-rabbit IgG antibody (Santa Cruz Biotechnology, USA) (1:3000) as a secondary antibody for 60 minutes at room temperature. The same amount of cellular proteins was confirmed by poly rabbit anti-(STAT1, STAT3) antibody. After incubation with antibodies, membrane was incubated with ECL solution (Millipore, Billerica, Mass., USA) and exposed to X-ray film. The amount of phosphorylated STAT-3 was measured in the band on the film.

The result shows that STAT-3 is phosphorylated by the treatment of IL-6 and the amount of phosphorylated STAT-3 is decreased by the pre-treatment of EC-18 in a concentration-dependent manner (FIG. 1A). FIG. 1B shows that the inhibitory effect of EC18 on STAT-3 phosphorylation is maintained after 1 hour.

Experimental Example 2

Inhibitory Effect of EC-18 on STAT-3 Phosphorylation in NK-92 Cells

Cells treated in EC-18 and PMA (Phobol 12-myristate 13-acetate) were lysed with cold SDS lysis buffer [(50 mM HEPES, 150 mM NaCl, 0.2 mM EDTA, 0.5% NP-40, 0.1% SDS, 1 mM $Na_3VO_4$, 10 mM NaF, and complete Protein Inhibitor Cocktail (Roche)] for 30 minutes on ice. After cell lysis, the aqueous solution was separated from the insoluble precipitate by centrifuging the cell lysates for 30 minutes at 13,000 rpm in a high-speed centrifuge. After protein quantification, the aqueous solution was separated in 10 to 12% SDS-PAGE by electrophoresis. Proteins separated in the gel were transferred into PVDF membrane (Millipore, Billerica, Mass., USA) at 100V for 2 hours.

To measure the amount of phosphorylated STAT-3 and STAT-1, the membrane was incubated with poly rabbit-anti-STAT3, poly rabbit-anti-STAT1, or poly rabbit-anti-phospho-STAT3 antibody (Cell Signaling Technology, USA (1:1000) as a primary antibody for 60 minutes at room temperature. The membrane was incubated with horseradish peroxidase-conjugated goat anti-rabbit IgG antibody (Santa Cruz Biotechnology, USA) (1:3000) as a secondary antibody for 60 minutes at room temperature. The same amount of cellular proteins was confirmed by poly rabbit anti-STAT3. After incubation with antibodies, membrane was incubated with ECL solution (Millipore, Billerica, Mass., USA) and exposed to X-ray film. The amount of phosphorylated STAT was measured in the band on the film.

The result shows that STAT-3 is phosphorylated by the treatment of IL-6 in NK-92 cells and the amount of phosphorylated STAT-3 is decreased by the pre-treatment of EC-18 in a concentration-dependent manner (FIG. 2A). In contrast, the result shows that EC18 does not inhibit STAT-1 phosphorylation (FIG. 2B).

Experimental Example 3

Measurement of Inhibitory Effect of EC-18 on STAT-3 Phosphorylation Using the Luciferase Reporter The pGL4.47 [luc2P/SIE/Hygro] vector (Promega) containing the sis-Inducible Element (SIE) that STAT-3 binds to was introduced into A549 cells and HepG2 cells. Inhibition of the STAT-3 activation by EC-18 was measured by pre-treating the cells with EC-18 and then treating the cells with IL-10.

After disrupting cells by treatment with trypsin-EDTA, A549 cells and HepG2 cells were split to the culture plate. Using Attractene Transfection Reagent (Qiagen), cells were transfected with pGL4.47 [luc2P/SIE/Hygro] vector and incubated at 37° C. under 5% $CO_2$ conditions for a day. In the next day, the cells were collected from the culture plate and 0.1 ml of cells were transferred to 96-well plate in a concentration of $5 \times 10^4$ cells/well and incubated at 37° C. under 5% $CO_2$ conditions for a day. In the next day, the cells were pre-treated with different concentrations of EC-18 for one hour and then treated with 10 ng/ml of IL-10. After incubation at 37° C. under 5% $CO_2$ conditions for 6 hours, Luciferease activity was measured using ONE-Glo Luciferase Assay System (Promega). Specifically, 0.1 ml of a 1:1 mixture of ONE-Glo Luciferase Assay System and Substrate was added to each well. After three minutes, the fluorescence was measured using VICTOR X Multilabel Plate Reader (PerkinElmer) during 0.5 second.

Luciferase fluorescence is decreased in cells pre-treated with different concentrations of EC-18, compared to cells treated with IL-10 alone, indicating decreased STAT-3 activity in cells pre-treated with EC-18 (FIG. 3A and 3B). The result shows that STAT-3 activation induced by IL10 is decreased by the treatment of EC-18 in A549 cells and HepG2 cells

Experimental Example 4

Efficacy of EC-18 for Treating Arthritis in Animal Model

For arthritis animal model experiment, arthritis was induced in male DBA/1J mouse by administering bovine type II collagen to the mouse. Efficacy of EC-18 for treating (or improving) arthritis was evaluated by repeatedly administering EC-18 to the mouse orally. For comparison, Remicade (positive control 1) was administered intraperitoneally and methotrexate (positive control 2) was administered orally. The experiment included seven groups: normal group (G1), negative control (G2), 125 mg/kg, 500 mg/kg and 2,000 mg/kg of EC-18 (EC-18 treatment groups, G3, G4, G5), 20 mg/kg of Remicade (Positive control 1, G6) and 2.5 mg/kg of Methotrexate (Positive control 2, G7). Each group consists of 10 mice. Olive oil was administered to normal group (G1) and negative control group (G2) as an excipient. In all groups, administration was made once a day for five weeks (a total of 35 administrations). Remicade (G6) was administered intraperitoneally, whereas EC-18, methotrexate and olive oil were administered orally in force. For all groups except normal Group (G1), arthritis was induced by immunizing animals twice with bovine type II collagen and complete Freund's adjuvant or incomplete Freund's adjuvant emulsion. During the observation period, common arthritis symptoms were observed once a day, weigh measured once a week, arthritic score evaluation made with the naked eye twice a week, foot thickness measured twice a week.

The concentration of IL-6 in serum collected at the day of tissue excision is shown in FIG. 4. As shown in FIG. 4, the concentration of IL-6 is significantly increased in Group 2 (negative control group) in which arthritis is induced by collagen and the concentration of IL-6 is reduced in EC-18 treatment groups (G3, G4 and G5), similar to the positive control groups (Remicade and Methothrexate treatment group, G6 and G7). FIG. 5 shows arthritis score evaluated by the examination with naked eye. As shown in FIG. 5, arthritis score in EC-18 treatment groups (G3, G4 and G5) is significantly decreased, compared to the negative control group (G2). FIG. 6 shows arthritis score measured by the histopathological examination of the extracted knee joint of both hind legs. As shown in FIG. 6, histopathological arthritis score is high in Group 2 (negative control group) in which arthritis is induced by collagen and the score is reduced in EC-18 treatment groups (G3, G4 and G5), similar to the positive control groups (Remicade and Methothrexate treatment group, G6 and G7). FIGS. 7 and 8 show microscopic images of stained arthritic tissue of normal group (G1), negative control group (G2), 500 mg/kg EC-18 treatment group (G4) and Remicade treatment group (G6) (FIG. 7; 40×, FIG. 8: ×100). As shown in FIGS. 7 and 8, crushing of cartilage and increase of Pannus are reduced in EC-18 treatment group (G4) and Remicade treatment group (G6), compared to the negative control group (G2). Thus, in this example, arthritis model was established as arthritis indexes such as arthritis score evaluated with naked eye, foot thickness, interleukin-6 (IL-6) level in serum, the concentration of anti-type II collagen (anti-CII)IgG and histopathological arthritis score are significantly increased in the negative control group, compared to the normal group. In addition, the results show that EC-18 is effective in treating arthritis.

From the above description, a person skilled in the art will appreciate that the invention may be embodied in other specific forms without changing the technical spirit or essential characteristics. In this regard, the examples described above are intended to be illustrative in all respects and it should be understood as not limiting. The scope of the invention should be understood to include all ranges of the above detailed description and the appended claims, rather than the ranges of the specific examples, as well as all such modifications derived from those equivalents.

The invention claimed is:

1. A method for preventing or treating rheumatoid arthritis by inhibiting phosphorylation of STAT-3, comprising administering to a patient in need thereof an effective amount of a compound of Formula 2:

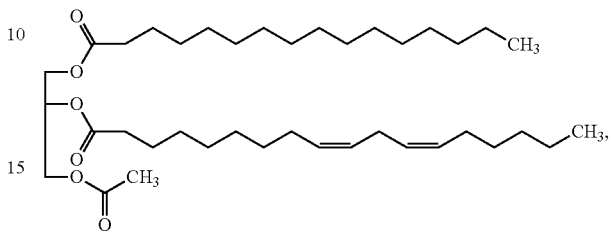

Formula 2 to inhibit phosphorylation of STAT-3 to thereby effect treatment of rheumatoid arthritis.

2. The method of claim 1 wherein the compound of Formula 2 is administered in a pharmaceutical composition which is substantially free of other monoacetyl diacyl glycerol compounds.

3. The method of claim 2 wherein the compound of Formula 2 is administered in a pharmaceutical composition which is substantially free of other triglyceride compounds.

4. The method of claim 1 wherein the patient in need experienced or is experiencing a side effect of a chemotherapeutic agent for the treatment of rheumatoid arthritis.

5. The method of claim 1 wherein the patient in need is a non-human.

6. The method of claim 2, wherein the pharmaceutical composition may be formulated into solid, liquid, gel or suspension form for oral or non-oral administration.

7. The method of claim 6 wherein the compound of Formula 2 is administered in the form of a pharmaceutical composition for oral administration.

8. The method of claim 7 wherein the compound of Formula 2 is administered in the form of a pharmaceutical composition which is a soft gelatin capsule containing the compound of Formula 2 in combination or association with a pharmaceutically acceptable diluent or carrier.

9. The method of claim 7 wherein the compound of Formula 2 is administered once or several times a day, at a total daily dosage of 0.001 to 1000 mg/kg body weight.

10. The method of claim 9 wherein the compound of Formula 2 is administered once or several times a day, at a total daily dosage of 0.05 to 200 mg/kg body weight.

11. The method of claim 10 wherein the compound of Formula 2 is administered once or several times a day, at a total daily dosage of 0.1 to 100 mg/kg body weight.

* * * * *